(12) United States Patent
Lee et al.

(10) Patent No.: US 9,096,872 B2
(45) Date of Patent: Aug. 4, 2015

(54) RECOMBINANT MICROORGANISMS HAVING INCREASED ABILITY TO PRODUCE BUTANOL AND METHOD OF PRODUCING BUTANOL USING THE SAME

(75) Inventors: Sang Yup Lee, Daejeon (KR); Yu-Sin Jang, Daejeon (KR); Jin Young Lee, Incheon (KR); Joung Min Lee, Gangwon-do (KR); Jin Hwan Park, Daejeon (KR)

(73) Assignees: KOREA ADVANCED INSTITUTE OF SCIENCE AND TECHNOLOGY (KR); BIOFUELCHEM CO. (KR); GS CALTEX CORPORATION (KR)

( * ) Notice: Subject to any disclaimer, the term of this patent is extended or adjusted under 35 U.S.C. 154(b) by 100 days.

(21) Appl. No.: 13/497,743

(22) PCT Filed: Sep. 21, 2010

(86) PCT No.: PCT/KR2010/006511
§ 371 (c)(1),
(2), (4) Date: Sep. 13, 2012

(87) PCT Pub. No.: WO2011/037415
PCT Pub. Date: Mar. 31, 2011

(65) Prior Publication Data
US 2013/0017588 A1    Jan. 17, 2013

(30) Foreign Application Priority Data
Sep. 22, 2009 (KR) .................. 10-2009-0089829

(51) Int. Cl.
*C12N 1/21* (2006.01)
*C12P 7/16* (2006.01)
*C12N 9/04* (2006.01)
*C12N 9/10* (2006.01)

(52) U.S. Cl.
CPC ............... *C12P 7/16* (2013.01); *C12N 9/0006* (2013.01); *C12N 9/1029* (2013.01); *C12Y 101/01001* (2013.01); *C12Y 203/01008* (2013.01); *C12Y 203/01019* (2013.01); *Y02E 50/10* (2013.01)

(58) Field of Classification Search
None
See application file for complete search history.

(56) References Cited

FOREIGN PATENT DOCUMENTS

WO       2008052973 A2     5/2008
WO    WO 2008/143704     * 11/2008

OTHER PUBLICATIONS

Nair et al. J. Bacteriol. (1994), 176(3) 871-885.*
Girbal, et al., "Regulation of solvent production in *Clostridium acetobutylicum*," Trends in Biotechnology., 1998, pp. 11-16, vol. 16.
Green, et al., "Genetic manipulation of acid formation pathways by gene inactivation in *Clostridium acetobutylicum* ATCC 824," Microbiology, 1996, pp. 2079-2086, vol. 142.
Jiang, et al., "Disruption of the acetoacetate decarboxylase gene in solvent-producing *Clostridium acetobutylicum* increases the butanol ratio," Metabolic Engineering, 2009, pp. 284-291, vol. 11.
Lee, et al., "Fermentative Butanol Production by Clostridia," Biotechnology and Bioengineering, 2008, pp. 209-228, vol. 101.
Nolling, et al., "Genome Sequence and Comparative Analysis of the Solvent-Producing Bacterium *Clostridium acetobutylicum*," Journal of Bacteriology, 2001, pp. 4823-4838, vol. 183.
Nair, et al., "Expression of Plasmid-Encoded aad in *Clostridium acetobutylicum* M5 Restores Vigorous Butanol Production," Journal of Bacteriology, 1994, pp. 5843-5846, vol. 176.
Scotcher, et al., "Sequences affecting the regulation of solvent production in *Clostridium acetobutylicum*," J. Ind. Microbiol Biotechnol, 2003, pp. 414-420, vol. 30.
Kuit, et al., Disruption of the acetate kinase (ack) gene of *Clostridium acetobutylicum* results in delayed acetate production, Applied Microbiol Biotechnol., 2012, vol. 94, pp. 729-741.
Lehmann, et al., Modifying the product pattern of *Clostridium acetobutylicum*, Applied Microbiol Biotechnol., 2012, vol. 94, pp. 743-754.
Cooksley, et al., Targeted mutagenesis of the *Clostridium acetobutylicum* acetone-butanol-ethanol fermentation pathway, Metabolic Engineering, 2012, vol. 14, pp. 630-641.
Jang, et al., Enhanced butanol production obtained by reinforcing the direct butanol-forming route in *Clostridium acetobutylicum*, mBio, 2012, vol. 3, 1-9 and supplementary materiels.

* cited by examiner

*Primary Examiner* — Nashaat Nashed
(74) *Attorney, Agent, or Firm* — Tristan A. Fuierer; Moore & Van Allen, PLLC

(57) ABSTRACT

The present invention relates to recombinant microorganisms having an increased ability to produce butanol, and a method of producing butanol using the same. More specifically, the invention relates to recombinant microorganisms whose ability to produce butanol was increased by manipulation of their metabolic networks, and a method of producing butanol using the same. The recombinant microorganisms having an increased ability to produce butanol comprise a deletion of a gene, which encodes an enzyme that converts acetyl CoA to acetate, in host microorganisms having genes that encode enzymes involved in acetyl CoA and butyryl CoA biosynthetic pathway. The recombinant microorganisms obtained by manipulating the metabolic flux of microorganisms are able to selectively produce butanol with high efficiency, and thus are useful as microorganisms for producing industrial solvents and transportation fuels.

2 Claims, 3 Drawing Sheets

RECOMBINANT MICROORGANISMS HAVING INCREASED ABILITY TO PRODUCE BUTANOL AND METHOD OF PRODUCING BUTANOL USING THE SAME

CROSS-REFERENCE TO RELATED APPLICATIONS

This application is filed under the provisions of 35 U.S.C. §371 and claims the priority of International Patent Application No. PCT/KR2010/006511 filed on 21 Sep. 2010 entitled "Recombinant Microorganisms Having Increased Ability to Produce Butanol and Method of Producing Butanol Using the Same" in the name of Sang Yup LEE, et al., which claims priority of Korean Patent Application No. 10-2009-0089829 filed on 22 Sep. 2009, both of which are hereby incorporated by reference herein in their entirety.

TECHNICAL FIELD

The present invention relates to recombinant microorganisms having an increased ability to produce butanol, and a method of producing butanol using the same. More specifically, the present invention relates to recombinant microorganisms whose ability to produce butanol was increased by manipulation of their metabolic networks, and a method of producing butanol using the same.

BACKGROUND ART

The recent rise in oil prices has caused an increased interest in alternative fuels such as biofuel. Also, butanol, a gasoline alternative having excellent physical properties compared to ethanol, is of increasing interest, and thus *Clostridium* sp. strains which produce solvents such as butanol as metabolites are also of increasing interest.

It is known that the microorganisms of the genus *Clostridium* are gram-positive, strictly anaerobic, endospore-forming bacteria and mostly produce acetic acid and butyric acid as fermentation products. Among them, some strains cause acetone-butanol-ethanol fermentation (hereinafter referred to as ABE fermentation) which produces acetone, butanol and ethanol in addition to the above organic acids.

Indeed, in the early 20$^{th}$ century, *Clostridium acetobutylicum* that is one of such strains was used to produce acetone and butanol in large amounts. This mass production was continued up to the 1960s and 1970s, but was discontinued except for some countries, because acetone and butanol produced from crude oils were inexpensive due to the development of chemical processes and it was difficult to supply substrates.

The production of biobutanol which has been performed to date using *Clostridium* sp. strains entails the following problems. First, it shows significantly low yield and productivity compared to the production of bioethanol based on yeast. Second, the *Clostridium* sp. strains produce, in addition to butanol that is highly valuable as biofuel, byproducts, including acetone, acetic acid and butyric acid, which increase their separation costs.

In *Clostridium* sp. strains that produce solvents, the productions of organic acids occurs at the exponential growth phase, like general microbial fermentation. It is referred to as the acidogenic phase. As the stationary phase approaches, the metabolism of cells shifts to the solventogenic phase in which organic acids are reassimilated and solvents such as acetone (or isopropanol), butanol and ethanol are produced. This can be interpreted as follows. As the stationary phase approaches, the pH decreases, and thus the concentration of non-dissociated organic acids increases. Among these acids, non-dissociated butyric acid shows high cytotoxicity. Through this reassimilation of organic acid and conversion into solvents, cells gain time to form endospores that can survive for a long period of time in a severe environment.

In wild-type strains, acetone, butanol and ethanol are produced at a mass ratio of about 3:6:1 after fermentation, and trance amounts of acetate, butyrate and acetoin are also produced. It is known that when glucose is used as a substrate, butanol is produced with a mass yield of about 20-25% at a final concentration of about 10 g/L (Lee et al., Biotechnol. Bioeng., 101(2):209-228, 2008). When such wild-type strains are used to produce butanol, there are problems in that yield and productivity are low and butanol is difficult to separate from other metabolites, thus increasing the production costs.

For this reason, in recent years, efforts have been made to make improved strains using metabolic engineering approaches, which manipulate metabolic pathways as desired, based on genetic engineering knowledge and tools. For *Clostridium acetobutylicum*, the pathways that produce metabolites have been known for a long time, and the genome was sequenced while genes corresponding thereto were all identified (Nolling et al., J. Bacteriol. 2001).

A metabolite that is most problematic in butanol production is acetone. If gas stripping is used for solvent separation, acetone and butanol are separated as mixtures because they are all easily evaporated, unlike organic acids, and an additional separation process is required. Acetoacetyl-CoA is converted to acetone by CoA transferase and acetoacetate decarboxylase. These enzymes are expressed by the genes ctfAB and adc, respectively. Thus, the concentration of acetone in solvents can be reduced by deleting one or more of these genes. According to a recent report, it was found that the deletion of adc can reduce the concentration of acetone can indeed the ratio of acetone (Jiang et al., Metab. Eng., 11(4-5):284-291, 2009).

Also, in the case of *Clostridium*, there is an example in which pta, a gene expressing phosphotransacetylase that is an enzyme of the acetate-producing pathway, and buk, a gene expressing butyrate kinase, were deleted by insertion of a plasmid by single crossover (Green et al., Microbiology. 142: 2079-2086, 1996). However, it was reported that, when the buk gene that encodes butyrate kinase was deleted, the concentration of butanol was increased to about 16 g/l, but when the pta gene that encodes phosphotransacetylase was deleted, the concentration of butanol was 9.9 g/l, indicating that the concentration of butanol and the selectivity for butanol did not substantially increase.

WO2008/052973 discloses a strain wherein the butyrate-producing pathway and the acetate-producing pathway are blocked and a strain wherein the butyrate-producing pathway, the acetone-producing producing pathway and the acetate-producing pathway are blocked. However, it is essential to block the butyrate-producing pathway, and thus it is impossible to determine whether the ability to produce butanol is increased when the acetate-producing pathway alone is deleted. In addition, WO2008/052973 discloses deletions of various combinations of genes based on a deletion of buk or ptb, but the examples thereof show only the already known results obtained by deleting the buk gene, and this patent document discloses an example relating to deletions of various combinations of genes. In other words, this patent document generally suggests only the possible deletions of various combinations of genes based on the buk or ptb deletion without providing a scientific experimental basis, but it is impossible to determine whether these deletions contribute to increases in concentration, yield, selectivity and the like in actual butanol production.

Thus, according to reports known to date, there is no evidence that the pta deletion is helpful in increasing the concentration and yield of butanol. In addition, because there is no information on the pta deletion, it is unclear what is the expected outcome if buk is deleted in a pta-deleted mutant strain. Also, if both the buk gene involved in the production of butyrate and the pta gene involved in the production of acetic acid are deleted, it can be expected that butyrate or acetic acid will not be produced, and thus the yield of butanol will increase (WO2008/052973), but this is an incorrect expectation (see the detailed description below).

Accordingly, the present inventors have found that, when a gene encoding an enzyme that converts acetyl CoA to acetate is deleted in the microorganisms of the genus *Clostridium*, the selectivity and yield of butanol are increased, indicating that the ability of the microorganisms to produce butanol is increased, thereby completing the present invention.

Furthermore, the present inventors have constructed microorganisms, which produce butanol at high concentration with high yield and selectivity, by deleting the buk gene in a pta-deleted mutant strain having improved butanol selectivity and yield and amplifying aldehyde/alcohol dehydrogenase in the mutant strain, and have found that the constructed microorganisms are able to produce butanol at high concentration with high yield and high selectivity, thereby completing the present invention.

Moreover, the present inventors have constructed a strain, which produces butanol at high concentration with high yield and selectivity without substantially producing organic acid, by deleting the bukII gene, which encodes butyrate kinase, in the mutant strain in which both pta and buk were deleted and aldehyde/alcohol dehydrogenase was amplified, and have confirmed the ability of the strain to produce butanol, thereby completing the present invention.

In addition, the present inventors have constructed a strain, which produces butanol at high concentration with high yield and selectivity without substantially producing organic acid, by deleting the ctfB gene, which encodes CoA transferase (CoAT), in the mutant strain in which pta, buk and bukII were all deleted and aldehyde/alcohol dehydrogenase was amplified, and have confirmed the ability of the strain to produce butanol, thereby completing the present invention.

DISCLOSURE OF INVENTION

It is an object of the present invention to provide a recombinant microorganism which selectively produces butanol with high efficiency while reducing the production of byproducts, and a preparation method thereof.

Another object of the present invention is to provide a method of producing butanol using said recombinant microorganism.

To achieve the above objects, the present invention provides a method for preparing a recombinant microorganism having an increased ability to produce butanol, the method comprising deleting a gene, which encodes an enzyme that converts acetyl CoA to acetate, in a host microorganism having acetyl CoA and butyryl CoA biosynthetic pathway.

The present invention also provides a recombinant microorganism having an increased ability to produce butanol, wherein a gene encoding an enzyme that converts acetyl CoA to acetate is deleted in a host microorganism having acetyl CoA and butyryl CoA biosynthetic pathway.

The present invention also provides a recombinant microorganism having an increased ability to produce butanol, wherein a phosphotrans-acetylase-encoding gene (eutD or pta) or an acetate kinase-encoding gene (askA or ackA) is deleted in a microorganism of the genus *Clostridium*.

The present invention also provides rebombinant microorganisms *Clostridium acetobutylicum* ATCC 824 ΔeutD, *Clostridium acetobutylicum* ATCC 824 ΔeutD Δbuk Ppt-bAdh, *Clostridium acetobutylicum* ATCC 824 ΔeutD Δbuk PthlAdh*, *C. actobutylicum* ATCC 824 ΔeutD Δbuk ΔbukII PthlAdh* and *C. actobutylicum* ATCC 824 ΔeutD Δbuk ΔbukII ΔctfB PthlAdh*, which have an increased ability to produce butanol.

The present invention also provides a method for producing butanol, comprising the steps of: culturing said recombinant microorganism to produce butanol; and recovering the produced butanol from the culture medium.

Other features and embodiments of the present invention will be more apparent from the following detailed descriptions and the appended claims

BEST MODE FOR CARRYING OUT THE INVENTION

Figure 1:
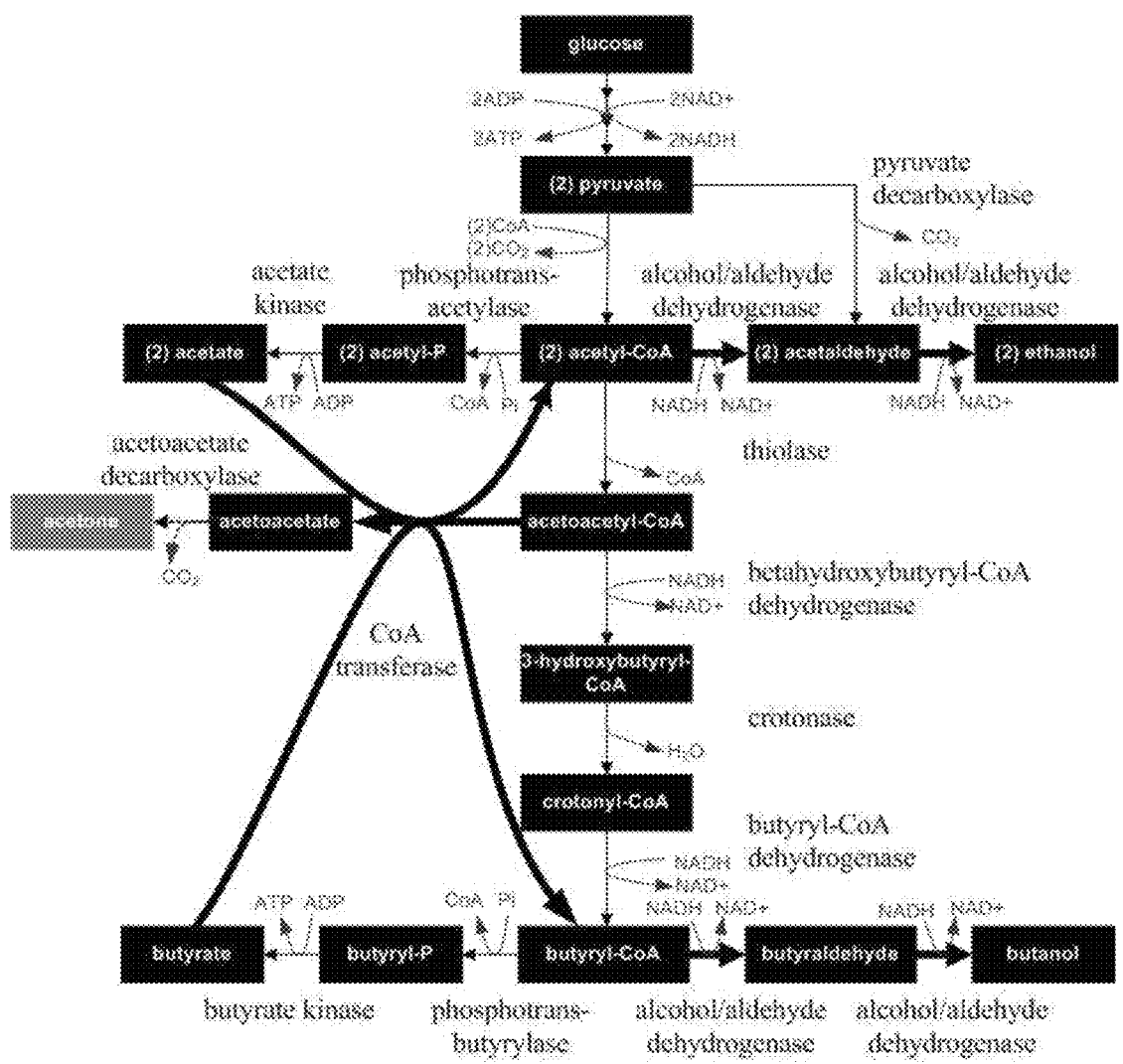
FIG. 1 is a metabolic network of a *Clostridium acetobutylicum* strain.
Figure 2:
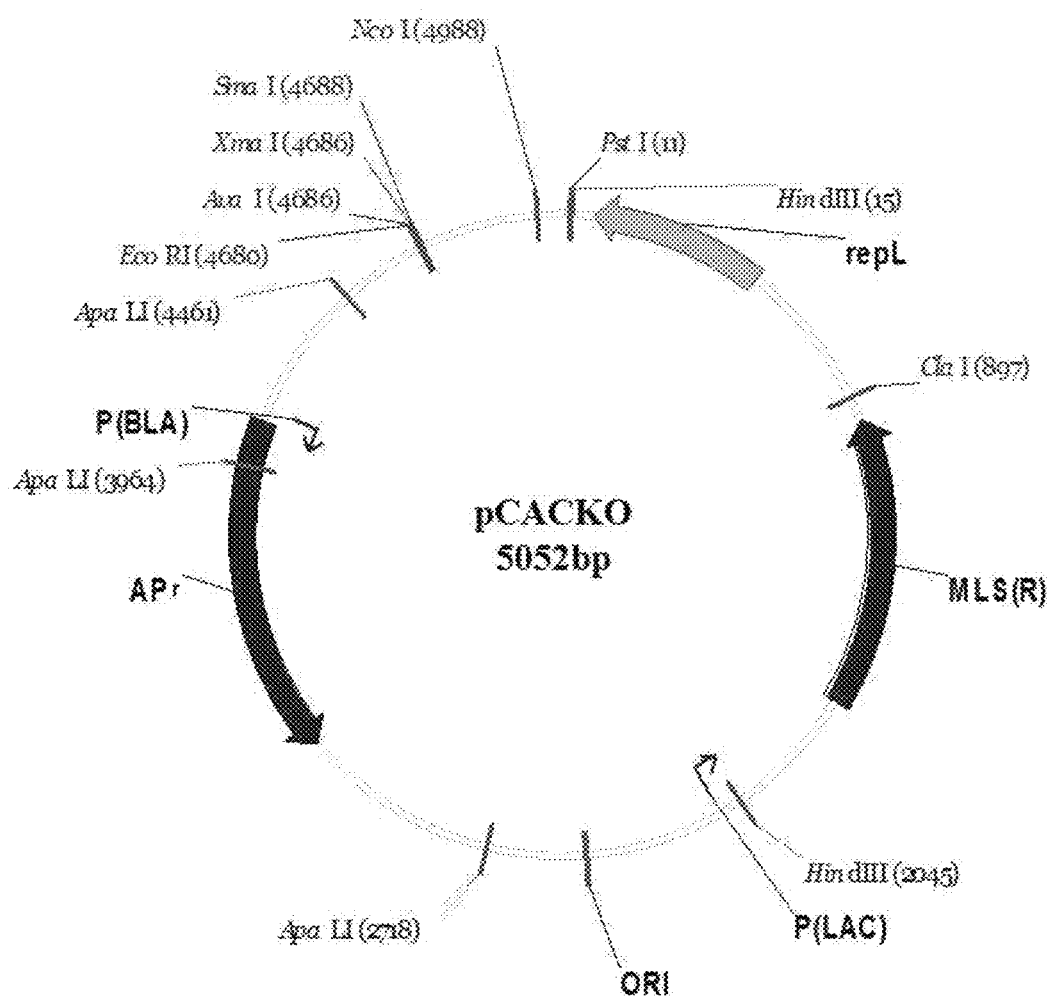
FIG. 2 is a genetic map of a gene-deleted vector (pCACKO) prepared according to one embodiment of the present invention.
Figure 3:
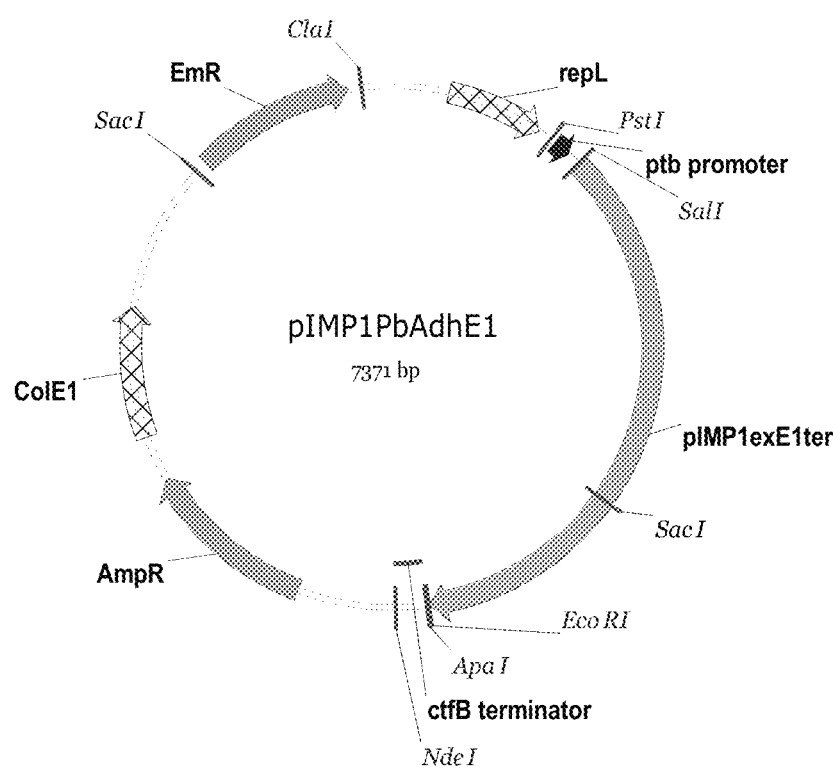
FIG. 3 is a genetic map of the plasmid pIMP1PbAdhE1 prepared according to one embodiment of the present invention.

In the present invention, the acetate synthetic pathway was deleted in the metabolic network of the *Clostridium acetobutylicum*, shown in FIG. 1, and whether the ability of the recombinant strain to produce butanol was increased was examined.

In one Example of the present invention, a recombinant microorganism was constructed by deleting a phosphotrans-acetylase-encoding gene, which is involved in converting acetyl CoA to acetate, from *Clostridium acetobutylicum* ATCC 824, and it was confirmed that the ability of the recombinant microorganism to produce butanol was increased.

In one aspect, the present invention is directed to a method for preparing a recombinant microorganism having an increased ability to produce butanol, the method comprising deleting a gene, which encodes an enzyme that converts acetyl CoA to acetate, in a host microorganism having acetyl CoA and butyryl CoA biosynthetic pathway, and a recombinant microorganism having an increased ability to produce butanol, which is prepared by said method.

As used herein, the term "biosynthetic pathway" is meant to include pathways in which a compound of interest is synthesized from a specific metabolite in a cell, without being limited only to pathways in which the compound of interest is synthesized from carbons provided through the relevant process (glycolysis).

As used herein, the term "deleted" is meant to include mutating, replacing or deleting part of the gene of interest, or introducing one or more bases into the gene, or introducing a gene, an enzyme or a chemical substance, which inhibits the expression or activity of the enzyme of interest, thereby inhibiting the activity of the enzyme. Thus, a method of deleting a specific gene is not limited to any particular method, so long as the activity of the specific gene of interest and the activity of the enzyme that is encoded by the gene is inhibited by conventional methods, including inhibition of expression by antisense RNA, homologous recombination, homologous recombination by expression of various recombinant enzymes (rambda recombinase, etc.), and insertion of a specific sequence using reverse transcriptase and RNA.

In the present invention, "having acetyl CoA and butyryl CoA biosynthetic pathway" means that not only a strain originally has the biosynthetic pathway, but also a foreign gene is introduced by techniques, including recombination and genome shuffling.

In the present invention, a host microorganism having acetyl CoA and butyryl CoA biosynthetic pathway may produce one or more selected from the group consisting of acetone, ethanol, butanol and isopropanol.

In the present invention, the host microorganism may be derived from the genus *Clostridium*, but is not limited thereto, so long as it has genes that encode enzymes involved in acetyl CoA and butyryl CoA biosynthetic pathway.

Examples of the microorganisms of the genus *Clostridium* include *Clostridium acetobutylicum, Clostridium beijerinckii, Clostridium saccharobutylicum, Clostridium saccharoperbutylacetonicum, Clostridium perfringens, Clostridium tetani, Clostridium difficile, Clostridium butyricum, Clostridium butylicum, Clostridium kluyveri, Clostridium tyrobutylicum, Clostridium tyrobutyricum*, and the like.

In the present invention, only *Clostridium acetobutylicum* ATCC 824 is illustrated as a host microorganism from the genus *Clostridium*, but *Clostridium acetobutylicum* M5, 1NYG, 4NYG, 5NYG and DG1 (Stim-Herndon, K. P. et al., *Biotechnol./Food Microbiol.*, 2:11, 1996), *Clostridium acetobutylicum* ATCC 824 Type IV, M3, M5, 2-BB R, 2-BB D, Rif B12, Rif D10, Rif F7, and *Clostridium acetobutylicum* ATCC 860 (Clark, S. W. et al., *Appl. Environ. Microbiol.*, 55:970, 1989) may also be used in the present invention.

In the present invention, the enzyme that converts acetyl CoA to acetate may be phosphotrans-acetylase or acetate kinase, the gene that encodes phosphotrans-acetylase may be eutD or pta, and the gene that encodes acetate kinase may be askA or ackA.

In the present invention, the method of deleting the gene is not specifically limited, so long as the activity of the enzyme that is encoded by the gene of interest is inhibited.

In one embodiment, in a method of homologous recombination by double crossover, an antibiotic resistance gene is inserted into a gene fragment having the base sequence of the gene of interest to inactivate the gene fragment, after which the inactivated gene fragment is introduced into a microbial strain such that double crossover recombination occurs between the gene of interest in the chromosome and the inactivated gene fragment, whereby the gene of interest in the chromosome of the microorganism.

In another embodiment, in a method of inserting a specific sequence using reverse transcriptase and RNA, a reverse transcriptase binding site is found in the gene of interest, after which part of RNA is inserted into the gene of interest by a complex of reverse transcriptase and an RNA expressed in an RNA transcription site replaced with a sequence adjacent to the binding site, whereby the activity of the enzyme of interest can be inhibited, thereby inactivating the gene of interest.

In one Example of the present invention, a recombinant microorganism in which a phosphotrans-acetylase-encoding gene (eutD) was deleted was constructed, and it was confirmed that the constructed recombinant microorganism has an increased ability to produce butanol.

In another Example of the present invention, a recombinant microorganism was constructed by (A) deleting a gene (ptb) or a gene (buk/bukII), which encode phosphotrans-butyrylase and butyrate kinase, respectively, which convert butyryl CoA to butyrate, in a recombinant microorganism in which a phosphotrans-acetylase-encoding gene (eutD) was deleted, and (B) amplifying aldehyde/alcohol dehydrogenase in the recombinant microorganism, and it was confirmed that the constructed recombinant microorganism has an increased ability to produce butanol and a decreased ability to produce acetone, butyrate and acetic acid. In addition, a recombinant microorganism in which (C) a ctfA or ctfB encoding CoA transferase (CoAT) was deleted was constructed, and it was confirmed that the constructed recombinant microorganism has the ability to butanol at high concentration with high yield and selectivity without substantially producing organic acid.

Thus, in the present invention, the method for preparing the recombinant microorganism having an increased ability to produce butanol comprises deleting one or more genes selected from the group consisting of (a) a gene encoding enzyme that converts acetate and butyrate to acetyl CoA and butyryl CoA, respectively, and converts acetoacetyl CoA to acetoacetate, (b) a gene encoding phosphotrans-butyrylase that converts butyryl-CoA to butyrate, and (c) a gene encoding butyrate kinase, in a microbial strain in which one or more of eutD (pta) and ackA genes, which encode phosphotrans-acetylase and acetate kinase, respectively, which convert acetyl-CoA to acetic acid, were deleted, and amplifying aldehyde/alcohol dehydrogenase in the strain.

The enzyme that converts acetate and butyrate to acetyl CoA and butyryl CoA, respectively, and converts acetoacetyl CoA to acetoacetate, is CoA transferase, and the gene that encodes CoA transferase is ctfAB or atoDA.

The gene encoding phosphotrans-butyrylase that converts butyryl-CoA to butyrate is ptb.

The gene encoding butyrate kinase is one or more selected from the group consisting of buk and bukII.

The gene encoding aldehyde/alcohol dehydrogenase is adhE1 or adhE2, and examples of the gene also include mutants thereof. Particularly, the mutants preferably contain one or more mutations in amino acid residues 450-650 of a protein (SEQ ID NO: 51) that is encoded by adhE1.

In still another Example of the present invention, a recombinant microorganism was constructed by deleting a gene (buk and/or bukII), which encodes an enzyme that converts butyryl CoA to butyrate, in a recombinant microorganism in which a phosphotrans-acetylase-encoding gene (eutD) was deleted, and a recombinant microorganism was constructed by additionally deleting ctfA or ctfB, which encodes CoA transferase, in the recombinant microorganism. In addition, a recombinant microorganism was constructed by introducing an alcohol/aldehyde dehydrogenase-encoding gene (adhE1) into the constructed recombinant microorganism. It was confirmed that the constructed recombinant microorganisms have an increased ability to produce butanol and a decreased ability to produce acetone.

Thus, the present invention relates to a method for preparing a recombinant microorganism, the method comprising deleting a gene encoding an enzyme that converts acetyl CoA and a gene encoding an enzyme that converts acetyl CoA to acetate, in a host microorganism having acetyl CoA and butyryl CoA biosynthetic pathway, and then introducing or amplifying one or more genes selected from the group consisting of genes that encode 1) alcohol dehydrogenase, 2) aldehyde dehydrogenase, and 3) alcohol/aldehyde dehydrogenase, in the host microorganism, and to a recombinant microorganism having an increased ability to produce butanol, prepared by the above method.

The gene encoding the enzyme that converts butyryl CoA to butyrate may be a phosphotrans-butyrylase-encoding gene (ptb) or a butyrate kinase-encoding gene (buk, bukII).

The present invention also relates to a method for preparing a recombinant microorganism, the method comprising deleting a gene, which encodes an enzyme that converts acetyl CoA to acetate, in a host microorganism having acetyl CoA and butyryl CoA biosynthetic pathway, and then additionally deleting a gene, which encodes an enzyme that converts butyryl CoA to butyrate, in the microorganism, additionally deleting a CoA transferase-encoding gene in the microorganism, and amplifying an alcohol/aldehyde dehydrogenase-encoding gene in the microorganism, and to a recombinant microorganism having an increased ability to produce butanol, prepared by the above method.

The alcohol dehydrogenase-encoding gene may be adh, the aldehyde dehydrogenase-encoding gene may be ald, and the alcohol/aldehyde dehydrogenase-encoding gene may be adhE1. The adhE1 gene may be amplified in various forms, thereby increasing the ability of the microorganism to produce butanol. Herein, the various forms include controlling the time point of expression and the level of expression using the ptb promoter, the buk promoter, the thl promoter or the like, including using a prototypic promoter, and also include mutant adhE1.

In another aspect, the present invention is relates to a recombinant microorganism having an increased ability to produce butanol, wherein a phosphotrans-acetylase-encoding gene (eutD or pta) or an acetate kinase-encoding gene (askA or ackA) is deleted in a microorganism of the genus *Clostridium*.

Examples of the recombinant microorganism having an increased ability to produce butanol include *Clostridium acetobutylicum* ATCC 824ΔeutD.

In still another aspect, the present invention is directed to a recombinant microorganism having an increased ability to produce butanol, wherein a phosphotrans-acetylase-encoding gene (eutD or pta) or an acetate kinase-encoding gene (askA or ackA) is deleted in a microorganism of the genus *Clostridium*, and a gene selected from the group consisting of 1) a butyrate transacetylase-encoding gene (ptb) or a butyrate kinase-encoding gene (buk and/or bukII) and 2) a CoA transferase-encoding gene (ctfAB or atoDA) is additionally deleted in the microorganism of the genus *Clostridium*.

Examples of the recombinant microorganism having an increased ability to produce butanol include *Clostridium acetobutylicum* ATCC 824ΔeutD Δbuk ΔbukII (*Clostridium acetobutylicum* ATCC 824ΔeutD Δbuk), *Clostridium acetobutylicum* ATCC 824ΔeutD Δbuk ΔctfB.

In yet another aspect, the present invention is directed to a recombinant microorganism having an increased ability to produce butanol, wherein a phosphotrans-acetylase-encoding gene (eutD or pta) or an acetate kinase-encoding gene (askA or ackA) is deleted in a microorganism of the genus *Clostridium*, and a gene selected from the group consisting of 1) a butyrate transacetylase-encoding gene (ptb) or a butyrate kinase-encoding gene (buk and/or bukII) and 2) a CoA transferase-encoding gene (ctfAB or atoDA) is additionally deleted in the microorganism of the genus *Clostridium*., and wherein aldehyde/alcohol dehydrogenase is amplified in the recombinant microorganism.

Examples of the recombinant microorganism having an increased ability to produce butanol include *Clostridium acetobutylicum* ATCC 824 ΔeutD Δbuk PptbAdh, *Clostridium acetobutylicum* ATCC 824 ΔeutD Δbuk Pth-lAdh*, and *Clostridium acetobutylicum* ATCC 824 ΔeutD Δbuk ΔbukII ΔctfB PthlAdh*.

In a further aspect, the present invention is directed to a method for producing butanol, comprising the steps of: culturing said recombinant microorganism to produce butanol; and recovering the produced butanol from the culture medium.

In the present invention, processes of culturing the recombinant microorganism and recovering ethanol and butanol can be performed using a conventional culture method and ethanol/butanol separation/purification method known in the fermentation industry. In addition, the recovery of butanol and ethanol is generally carried out after completion of the culture process, but ethanol and butanol may also be recovered during the culture process using the gas-stripping method (Thaddeus et al., *Bioprocess Biosyst. Eng.*, 27:207, 2005) or the like in order to increase the production of ethanol and butanol. In other words, carrying out the culture process while recovering ethanol and butanol produced during the culture process also falls within the present invention.

EXAMPLES

Hereinafter, the present invention will be described in further detail with reference to examples. It will be obvious to a person having ordinary skill in the art that these examples are illustrative purposes only and are not to be construed to limit the scope of the present invention.

Particularly, in the following examples, *Clostridium acetobutylicum* ATCC 824 was illustrated as a host strain from which a gene would be deleted according to the present invention. However, it will be obvious to a person skilled in the art that, even when other microorganisms of the genus *Clostridium* or microorganisms of other genera are used, the same gene is deleted in the host strain having acetyl CoA and butyryl CoA biosynthetic pathway, and the resulting strain is used to produce ethanol and butanol.

Example 1

Construction of Vector Comprising Mutant loxP Site and Antibiotic Resistance Marker In the case of *Clostridium acetobutylicum*, an erythromycin resistance gene (hereinafter referred to as Em$^r$) is mainly used as an antibiotic resistance marker for a vector. For gene deletion by double crossover recombination, an additional antibiotic resistance marker is required to select a strain in which a double crossover occurred. Thus, pSOS95-Cm that expresses a chloramphenicol/thiamphenicol resistance marker (hereinafter referred to as Th$^r$) using the thiolase promoter of *Clostridium acetobutylicum* was used as a template for PCR. pSOS95-Cm can be constructed by cloning the thioloase promoter of the ATCC 824 strain into pSOS95 (Nair and Papoutsakis, *J. Bacteriol.*, 176:5843-5846, 1994) and cloning a chloramphenicol/thiamphenicol resistance gene downstream of the promoter.

Also, after a gene was deleted by double crossover, the inserted antibiotic resistance marker should be removed for deletion of other genes. For this purpose, a mutant loxP sequence was added to primers used when amplifying Th$^r$ by PCR. Also, for ligation into a vector, the sequences GCATGC and TCTAGA of the restriction enzyme sites SphI and XbaI were added to the primers, respectively. The final primer sequences are shown by SEQ ID NOS: 1 and 2.

[SEQ ID NOS: 1]:
5-'AATTGCATGCTACCGTTCGTATAATGTATGCTATACGAAGT

TATCACACGGTTTAA CGACTTAATTACG-3'

[SEQ ID NOS: 2]:
5'-ATATTCTAGAACCGTTCGTATAGCATACATTATACGAAGTT

ATCCATGATTACGAA TTCTATGAGTCGAC-3'

PCR amplification was performed using the above template and primers, thus obtaining a PCR product comprising both the mutant loxP site and Th$^r$. The PCR product thus obtained and a pUC18 plasmid were digested with SphI/XbaI, and then ligated to each other, thus preparing the vector pMBKOT2. The vector pMBKOT2 was used in the construction of a KO cassette comprising the loxP-Thr-loxP portion and homologous arm of the pMBKOT2.

Example 2

Construction of pCACKO Vector

Gene deletion by homologous recombination is generally performed using a plasmid that is not replicated in cells. However, in the case of *Clostridium acetobutylicum*, it is known that the ratio of transformation is very lower than that in *E. coli*, and homologous recombination does not easily occur. For this reason, a replicable plasmid is preferably used. Thus, a vector that can delete a specific gene was constructed using the pMBKOT2 constructed in Example 1 and the shuttle vector pIMP1 (Nair and Papoutsakis, J. Bacteriol., 176:5843-5846, 1994) that is replicable in *Clostridium acetobutylicum*.

The restriction enzyme sequences in pIMP1 are not suitable, except for XmaI, because they digest the inside of the loxP-Th$^r$-loxP sequence of pMBKOT2. For this reason, the restriction enzyme sequence NcoI that is not present in both pMBKOT2 and pIMP1 was added to pIMP1. PCR amplification was performed using about 300 base pairs (1155-1468 of L08752.1) located in pUC18 (GenBank ID: L08752.1), as a template, with the following primers (SEQ ID NOS: 3 and 4). The base sequence of NcoI was included in the primer of SEQ ID NO: 3.

[SEQ ID NOS: 3]:
5'-AAAACTGCAGCCATGGTCGCCAGTTAATAGTTTGCG-3'

[SEQ ID NOS: 4]:
5'-AAAACCCGGGCGCCGCATACACTATTCTCA-3'

The PCR product thus obtained and pIMP1 were digested with NcoI/XmaI, and then ligated to each other, thus constructing a pCACKO vector. Based on this vector, a gene-deleted vector was constructed.

Test Example 1

Method of Deleting a Gene of Interest Using pCACKO

A gene of interest (eutD, ctfB, buk or bukII) together with a thiamphenicol marker was amplified and ligated into the pCACKO vector constructed in Example 2, and the vector was methylated and transformed by electroporation into the *C. actobutylicum* ATCC 824 strain (Mermelstein and Papoutsakis, Appl. Environ. Microbiol., 59(4):1077-1081, 1993).

The transformed strain was subcultured in 2xYTGS medium (16 g/L bacto tryptone, 10 g/L bacto yeast extract, 4 g/L NaCl, 2 g/L glucose, 15 g/L soluble starch, pH 6.8) while it was plated onto 2xYTG agar (16 g/L bacto tryptone, 10 g/L bacto yeast extract, 4 g/L NaCl, 5 g/L glucose, 15 g/L agar, pH 5.8) containing thiamphenicol.

Each of the colonies obtained from the plate was examined by colony PCR to confirm whether the Th$^r$ marker was successfully inserted into the ORF of the gene of interest. When recombination on both sides of gene surely occurred, the colony was cultured and plated, after a degeneration test was performed to confirm that pSOL1 involved in solvent production was not lost (Scotcher and Bennett, *J. Bacteriol.*, 187(6): 1930-1936, 2005). The resulting strain was subcultured more than 30 times in 2xYTGS medium in order to remove the used pCACKO vector, after which it was plated onto 2xYTG agar containing Th and was replicated on 2xYTG agar containing erythromycin (Em). Then, several colonies showing no Em$^r$ were selected, and then subjected to a degeneration test in the same manner as described above, and a colony in which pSOL1 was not lost was finally selected.

Test Example 2

Construction of Vector that Expresses Cre Recombinase

After the gene of interest was deleted in Test Example 1, a vector that expresses Cre recombinase was prepared in order to remove the thiamphenicol resistance gene that is the antibiotic resistance marker inserted in the gene. To make the vector that expresses Cre recombinase, an operation was performed using pSOS95 (GenBank ID:AY187686.1), which comprises the promoter of the thiolase gene of *C. acetobutylicum*, as a parent vector. The cre gene is not suitable for use, because a BamHI site is present in the ORF sequence of the gene. For this reason, a strand comprising a ribosome binding site and an XbaI site was amplified using the chromosomal DNA of *C. acetobutylicum* as a template with primers of SEQ ID NOS: 5 and 6. Then, the amplified product and pSOS95 were digested with BamHI/NarI, and then ligated to each other using T4 ligase, thereby constructing a pSOS95-X vector.

[SEQ ID NOS: 5]:
5'-GCATGGATCCAGAATTTAAAAGGAGGGATTAAATCTAGAA

TGATAAGAAGCATGACGGGATTTG-3'

[SEQ ID NOS: 6]:
5'-GCATGGCGCCTCACTCTATATTTTGAATTTGTTCTC-3'

In order to amplify the cre gene, PCR amplification was performed using pJW168 (Palmeros et al., Gene, 247:255~264, 2000)) as a template with primers of SEQ ID NOS: 7 and 8. Then, the amplified product and pSOS95-X were digested with XbaI/NarI, and then ligated to each other using T4 ligase, thereby constructing a pSOS95del-cre vector.

[SEQ ID NOS: 7]:
5'-GCAATCTAGAATGTCCAATTTACTGACCGTACA-3'

[SEQ ID NOS: 8]:
5'-GCATGGCGCCCTAATCGCCATCTTCCAGCAGG-3'

Test Example 3

Removal of Antibiotic Resistance Marker, Inserted into Gene, Using pSOS95del-cre pSOS95del-cre constructed in Example 2 was transformed by electropotation into the *C. actobutylicum* ATCC 824 recombinant strain in which the gene of interest was deleted in the same manner as described in Test Example 1. The transformed strain was subcultured 3-5 times in 2x YTGS medium, and then plated onto 2xYTG agar. As colonies grew, they were replicated on 2x YTG agar containing Th, and colonies that lost $Th^r$ were selected. Then, the selected colonies were examined by colony PCR using the internal/external primers of the deleted gene in order to confirm the removal of the $Th^r$ based on the difference of the length of the amplified gene.

The colonies thus selected were subjected to a degeneration test as described in Test Example 1, and colonies in which pSOL1 was not lost were selected. The verified colonies were subcultured in the same manner as described in Test Example 1, and a colony that lost pSOS95del-Cre without losing pSOL1 was selected. The strain obtained according to the above method has no antibiotic resistance marker, and thus can be used in performing the deletion of other genes, without modifying the marker of the existing vector.

Example 3

Construction of Strain in which Acetate-Producing Pathway was Blocked

In order to delete the eutD gene involved in the acetate-producing pathway, strands (1890304-1890770 and 1890831-1891380 of NCBI RefSeq ID: NC_003030.1) comprising the ORF of eutD were amplified using a primer pair of SEQ ID NOS: 9 and 10 and a primer pair of SEQ ID NOS: 11 and 12, respectively. Herein, as the sequences to be amplified, templates having no NcoI and XmaI were selected. It was found that the two portions of the ORF contained in each of the amplified products did not overlap with each other and had the same orientation. Also, in order to insert a marker between the two strands, part of pMBKOT2 comprising loxP-$Th^r$-loxP was amplified using primers of SEQ ID NOS: 13 and 14.

```
[SEQ ID NOS: 9]:
5'-CTAGCCATGGAGCATATGGGAGTGTGCTAAG-3'

[SEQ ID NOS: 10]:
5'-CGGCCAACGCTCGCAGTCAGGTATTATCAT-3'

[SEQ ID NOS: 11]:
5'-GCGAATGGCGAGATGAACTAGCTGATATTGCTATAA-3'

[SEQ ID NOS: 12]:
5'-ACGTCCCGGGCGAGTACAGTTTCATCCTTCATATC-3'

[SEQ ID NOS: 13]:
5'-CTGACTGCGAGCGTTGGCCGATTCAT-3'

[SEQ ID NOS: 14]:
5'-TAGTTCATCTCGCCATTCGCCATTCA-3'
```

Overlapping PCR was performed using the three amplified strands as a template with primers of SEQ ID NOS: 9 and 12, thereby obtaining one strand. The final PCR product thus obtained and the pCACKO (KO vector) prepared in Example 2 were digested with NcoI/XmaI, and then ligated to each other, thereby constructing a pCACKO-eutD vector. The constructed vector was methylated, and then transformed by electroporation into the *C. actobutylicum* ATCC 824 strain. The transformed strain was subcultured in 2x YTGS medium while it was plated onto 2x YTG agar containing thiamphenicol. The colonies obtained from the plate were examined by colony PCR with each primer pair of SEQ ID NOS: 16 and SEQ ID NO: 17 and 18 in order to confirm whether the $Th^r$ marker was successfully inserted in the eutD ORF.

```
[SEQ ID NOS: 15]:
5'-GAGGATAAAGAATATACGCAGG-3'

[SEQ ID NOS: 16]:
5'-TTGCCGTCCTAAACTCTGAA-3'

[SEQ ID NOS: 17]:
5'-CTTCCTTTGGCAATTCAAGTTC-3'

[SEQ ID NOS: 18]:
5'-GTGGATTATGAAGCGGTGCA-3'
```

When recombination on both sides of the gene surely occurred, the colony was cultured and plated, after which it was subjected to a degeneration test in order to verify that pSOL1 involved in solvent production was not lost. The verified strain was subcultured more than 30 times in 2×YTGS medium, after which it was plated onto 2x YTG agar containing Th and was replicated on 2x YTG agar containing erythromycin (Em), and several colonies showing no $Em^r$ were selected. The selected colonies were subjected to a degeneration test in the same manner as described above, and a colony in which pSOL1 was not lost was finally selected.

Then, pSOS95del-cre was transformed into the finally selected strain in the same manner as described in Test Example 3 to remove the thiamphenicol resistance gene inserted in the gene. The strain was subcultured to remove pSOS95del-cre, thereby preparing a final strain (*Clostridium acetobutylicum* ATCC 824 ΔeutD) which is sensitive to antibiotics, such as thiamphenicol and erythromycin, like a wild-type strain, and in which the eutD gene was deleted.

Example 4

Development of Recombinant Strain by Additional Gene Deletion and Gene Amplification In order to delete one or more genes selected from buk, bukII and ctfB in the *Clostridium acetobutylicum* ATCC 824 ΔeutD strain, the genes were deleted in the strain (*Clostridium acetobutylicum* ATCC 824 ΔeutD) as host microorganisms, prepared in Example 2, in the same manner as described in Example, thereby preparing recombinant microorganisms. In addition, the adhE1 gene of *C. acetobutylicum* ATCC 824, which expresses alcohol/aldehyde dehydrogenase, was introduced into the corresponding strains.

For deletion of additional genes, the following sequences of SEQ ID NOS: 19 to 36 were used. Specifically, for deletion of the buk gene, sequences of SEQ ID NOS: 19 to 24 were used, and for deletion of the bukII gene, sequences of SEQ ID NOS: 25 to 30 were used. In addition, for deletion of the ctfB gene, sequences of SEQ ID NOS: 31 to 36 were used.

[SEQ ID NOS: 19]:
5'-CTAGCCATGGATGTATAGATTACTAATAATC-3'

[SEQ ID NOS: 20]:
5'-CGGCCAACGCCTATTTCATTTGCAATAATTC-3'

[SEQ ID NOS: 21]:
5'-GCGAATGGCGCCAAGAAAAAGTATATTCCATG-3'

[SEQ ID NOS: 22]:
5'-ACGTCCCGGGCTTCTCCTCTTAAAACTCTAAG-3'

[SEQ ID NOS: 23]:
5'-ATTGCAAATGAAATAGCGCCATTCGCCATTCA-3'

[SEQ ID NOS: 24]:
5'-TATACTTTTTCTTGGGCGTTGGCCGATTCAT-3'

[SEQ ID NOS: 25]:
5'-CTAGCCATGGGGACTTTATTATGAAATTTAAAC-3'

[SEQ ID NOS: 26]:
5'-CGGCCAACGCCACTATATATGCTGACACTCC-3'

[SEQ ID NOS: 27]:
5'-GCGAATGGCGCTGGAATACCTGAACTTCCTAG-3'

[SEQ ID NOS: 28]:
5'-ACGTCCCGGGAACCCTTAAGGTTCCTTCTGC-3'

[SEQ ID NOS: 29]:
5'-GTCAGCATATATAGTGCGCCATTCGCCATTCA-3'

[SEQ ID NOS: 30]:
5'-AGTTCAGGTATTCCAGGCGTTGGCCGATTCAT-3'

[SEQ ID NOS: 31]:
5'-CTAGCCATGGTCCCTATATGGCAATGGCAGC-3'

[SEQ ID NOS: 32]:
5'-CGGCCAACGCTTAGGACTAGCGCCCATTCC-3'

[SEQ ID NOS: 33]:
5'-GCGAATGGCGGGAGGAGACTATACAACAGTAC-3'

[SEQ ID NOS: 34]:
5'-ACGTCCCGGGTTCTTTCTAAACAGCCATGGGTC-3'

[SEQ ID NOS: 35]:
5'-GGGCGCTAGTCCTAACGCCATTCGCCATTCA-3'

[SEQ ID NOS: 36]:
5'-TTGTATAGTCTCCTCCGCGTTGGCCGATTCAT-3'

The adhE1 gene of C. acetobutylicum ATCC 824 was amplified by PCR using primers of SEQ ID NOS: 37 and 38. The PCR product was cloned between the ptb gene promoter and ctfB transcription terminator of the pIMPlexter vector. The PCR product and the pIMPlexter vector were digested with SalI/EcoRI restriction enzymes, and then ligated to each other. The ptb promoter of the pIMPlexter was amplified with primers of SEQ ID NOS: 39 and 40 and cloned into the PstI and SalI restriction enzyme sites of pIMP1 (Nair and Papoutsakis, J. Bacteriol., 176:5843-5846, 1994). The terminator sequence was amplified using primers of SEQ ID NOS: 41 and 42 and cloned into the EcoRI and NdeI restriction enzyme sites of the vector into which the ptb promoter had already been cloned, thereby preparing pIMPlexter. pTHL-Adh* was constructed by linking a fragment amplified using primers of SEQ ID NOS: 43 and 44 and a fragment amplified using primers of SEQ ID NOS: 45 and 46 to a pTHL1-Cm vector by overlap PCR, and then cloning the fragments into the PstI and AvaI restriction enzyme sites of the vector. Mutant Adh* is an artificial recombinant protein prepared by cloning into a pTHL1-Cm vector an adhE1 fragment amplified using primers of SEQ ID NOS: 43 and 46, inducing a mutation in the fragment using NTG, followed by screening. In the screening of mutant Adh using NTG, those having one or more mutations in amino acid residues 450-650 of the amino acid sequence of SEQ ID NO: 51 increased the production of butanol. Adh* used in this Example was obtained by reproducing one at the highest frequency of variation in the library using sequence of SEQ ID NOS: 43 to 46.

[SEQ ID NOS: 37]:
5'-ATAGTCGACATGAAAGTCACAACAGTAAAGG-3'

[SEQ ID NOS: 38]:
5'-CGCGAATTCTTAAGGTTGTTTTTTAAAACA-3'

[SEQ ID NOS: 39]:
5'-TATCTGCAGTGTGGATGGAGTTAA-3'

[SEQ ID NOS: 40]:
5'-ATTGTCGACTTTAATCCCTCCTTT-3'

[SEQ ID NOS: 41]:
5'-CGCGAATTCGGGCCCATATCCAATGAACTTAGACC-3'

[SEQ ID NOS: 42]:
5'-CACCATATGGCCTAGAGCTGAAGTTAT-3'

[SEQ ID NOS: 43]:
5'-AAAACTGCAGTTTATGAAAGTCACAACAGTAAAGG-3'

[SEQ ID NOS: 44]:
5'-TAAATTATAGGGGTCACTACCAGTAACTATAAAGGCTC-3'

[SEQ ID NOS: 45]:
5'-GAGCCTTTATAGTTACTGGTAGTGACCCCTATAATTTA-3'

[SEQ ID NOS: 46]:
5'-CCCCCGGGGGGTTGAAATATGAAGGTTTAAGGTTG-3'

As a result, the following strains were prepared: Clostridium acetobutylicum ATCC 824 ΔeutD Δbuk ΔbukII, Clostridium acetobutylicum ATCC 824 ΔeutD Δbuk ΔctfB, Clostridium acetobutylicum ATCC 824 ΔeutD Δbuk PptbAdh, Clostridium acetobutylicum ATCC 824 ΔeutD Δbuk ΔbukII PthlAdh*, and Clostridium acetobutylicum ATCC 824 ΔeutD Δbuk ΔbukII ΔctfB PthlAdh*.

For reference, the pTHL1-Cm vector was prepared in the following manner.

A shuttle vector for foreign protein expression comprising the thiolase promoter and ribosome binding site (RBS) of Clostridium acetobutylicum was prepared in the following manner. It is known that thiolase can continuously and stably express a gene without being greatly influenced by the cell growth cycle (Tummala et al., Appl. Environ. Microbiol., 65:37933799, 1999). Thus, in this Example, the promoter at the top of thiolase (NCBI GeneID: 1119056) was cloned and inserted into pIMP-H1del. pIMP-H1del is a shuttle vector, which has pIMP1 as a template and is obtained by removing a HindIII site at position 3408 of pIMP1 having two HindIII restriction enzyme while leaving the restriction enzyme site at position 743 of pIMP1. The thiolase promoter was amplified by PCR using the total DNA of the Clostridium acetobutylicum ATCC 824 strain with primers of SEQ ID NOS: 47 and 48. The amplified thiolase promoter fragment was purified and recovered, after which it was treated with HindIII and PstI restriction enzymes and ligated with the pIMP-H1del shuttle vector treated with the same restriction enzymes, thereby constructing a pTHL1 vector.

[SEQ ID NOS: 47]:
5'-GGCCCCAAGCTTAGAATGAAGTTTCTTATGCACAAG-3'

[SEQ ID NOS: 48]:
5'-AAACTGCAGTCTAACTAACCTCCTAAATTTTGATAC-3'

In addition, a chloramphenicol resistance gene was amplified by PCR using pSOS95-Cm with primers of SEQ ID NOS: 49 and 50. The amplified gene fragment was purified and recovered, after which it was treated with a HindIII restriction enzyme and ligated with the pTHL1 shuttle vector treated with the same restriction enzyme, thereby constructing a pTHL1-Cm vector. pSOS95-Cm can be constructed by cloning the thioloase promoter of the ATCC 824 strain into pSOS95 (Nair and Papoutsakis, J. Bacteriol., 176:5843-5846, 1994) and cloning a chloramphenicol/thiamphenicol resistance gene downstream of the promoter.

[SEQ ID NOS: 49]:
5'-CCAAGCTTCGACTTTTTAACAAAATATATTG-3'

[SEQ ID NOS: 50]:
5'-CCAAGCTTGACATTAAAAAAATAAGAGTTACC-3'

[SEQ ID NOS: 51]:
MKVTTVKELDEKLKVIKEAQKKFSCYSQEMVDE

IFRNAAMAAIDARIELAKAAVLETGMGLVEDKVIKNHFAGEYIYNKYKDEKTCGIIERNE

PYGITKIAEPIGVVAAIIPVTNPTSTTIFKSLISLKTRNGIFFSPHPRAKKSTILAAKTI

LDAAVKSGAPENIIGWIDEPSIELTQYLMQKADITLATGGPSLVKSAYSSGKPAIGVGPG

NTPVIIDESAHIKMAVSSIILSKTYDNGVICASEQSVIVLKSIYNKVKDEFQERGAYIIK

KNELDKVREVIFKDGSVNPKIVGQSAYTIAAMAGIKVPKTTRILIGEVTSLGEEEPFAHE

KLSPVLAMYEADNFDDALKKAVTLINLGGLGHTSGIYADEIKARDKIDRFSSAMKTVRTF

VNIPTSQGASGDLYNFRIPPSFTLGCGFWGGNSVSENVGPKHLLNIKTVAERRENMLWFR

VPHKVYFKFGCLQFALKDLKDLKKKRAFIVTDSDPYNLNYVDSIIKILEHLDIDFKVFNK

VGREADLKTIKKATEEMSSFMPDTIIALGGTPEMSSAKLMWVLYEHPEVKFEDLAIKFMD

IRKRIYTFPKLGKKAMLVAITTSAGSGSEVTPFALVTDNNTGNKYMLADYEMTPNMAIVD

AELMMKMPKGLTAYSGIDALVNSIEAYTSVYASEYTNGLALEAIRLIFKYLPEAYKNGRT

NEKAREKMAHASTMAGMASANAFLGLCHSMAIKLSSEHNIPSGIANALLIEEVIKFNAVD

NPVKQAPCPQYKYPNTIFRYARIADYIKLGGNTDEEKVDLLINKIHELKKALNIPTSIKD

AGVLEENFYSSLDRISELALDDQCTGANPRFPLTSEIKEMYINCFKKQP

Example 5

Production of Alcohol Using Recombinant Strain

A 30-ml test tube containing 10 ml of CGM medium (Table 1) was sterilized, filled with nitrogen gas and cooled to room temperature in an anaerobic chamber. Then, the recombinant microorganism (*Clostridium acetobutylicum* ATCC 824 ΔeutD) prepared in Example 3 was inoculated into the test tube and precultured at 37° C. in anaerobic conditions until it reached an absorbance of 1.0 at 600 nm.

TABLE 1

| Components | Contents (g/l) |
|---|---|
| Glucose | 80 |
| K₂HPO₄3H₂O | 0.982 |
| KH₂PO₄ | 0.75 |
| MgSO₄ | 0.348 |
| MnSO₄H₂O | 0.01 |
| FeSO₄7H₂O | 0.01 |
| (NH₄)₂SO₄ | 2 |
| NaCl | 1 |
| asparagine | 2 |
| PABA (paraaminobenzoic acid) | 0.004 |
| Yeast extract | 5 |

A 500-ml flask containing 200 ml of CGM medium was sterilized and treated in the same manner as described above. Then, 8 ml of the above preculture broth was inoculated into the flask and further precultured at 37° C. in anaerobic conditions until it reached an absorbance of 1.0 at 600 nm. Then, a 5.0-L fermenter (LiFlus GX, Biotron Inc., Kyunggi-Do, Korea) containing 2.0 L of CGM medium was sterilized, after which the temperature was lowered from 80° C. or more to 37° C. while nitrogen was supplied to the fermenter at a flow rate of 0.5 vvm for 10 hours. Then, 200 ml of the secondarily precultured broth was inoculated into the fermenter and cultured at 37° C. and 200 rpm for 60 hours. The pH was maintained at 5.0 by automatically feeding 5N NaOH, and nitrogen was supplied at a flow rate of 0.2 vvm (air volume/working volume/minute) during the culture.

Glucose in the culture medium was measured by a glucose analyzer (model 2700 STAT, Yellow Springs Instrument, Yellow Springs, Ohio, USA), and the culture medium was collected at varying time points. The concentrations of acetone, ethanol and butanol in the collected medium were measured by gas chromatography (Agilent 6890N GC System, Agilent Technologies) equipped with a packed column column (Supelco Carbopack™ BAW/6.6% PEG20M, 2 m×2 mm ID, Bellefonte, Pa., USA), thereby measuring the production yields of the organic solvents. The results of the measurement are shown in Tables 2 and 3 below.

TABLE 2

| | Strains and productivity (g/l) | |
|---|---|---|
| Organic solvents | ATCC824⁺ | ΔeutD |
| Acetone | 4.3 | 6.6 |
| Ethanol | 0.5 | 2.9 |
| Butanol | 9.7 | 18.5 |
| Acetate | 6.4 | 4.3 |
| Butyrate | 5.7 | 0.9 |

⁺Data from Walter (1993)

TABLE 3

| | Yield (organic solvent/glucose) | |
|---|---|---|
| Organic solvents | ATCC824 | ΔeutD |
| Acetone | 0.25 | 0.24 |
| Ethanol | 0.05 | 0.13 |
| Butanol | 0.17 | 0.21 |

As can be seen in Tables 2 and 3 above, the control wild-type *Clostridium acetobutylicum* ATCC 824 showed a butanol productivity of less than 10 g/L, whereas the recombinant microorganism *Clostridium acetobutylicum* ATCC824 ΔeutD prepared in Example 3 showed increased butanol concentration and yield, indicating that it has an increased ability to produce butanol. In addition, it could be seen that not only the final concentrations of ethanol and butanol, but also the yields were increased.

Example 6

Comparison of Abilities of Recombinant Strains to Produce Butanol

The fermentation of the *C. actobutylicum* ATCC 824 and recombinant strains shown in Table 4 below was performed under the same conditions as those in Example 5.

TABLE 4

| Strains | Butanol concentration (g/L) | Butanol yield (g/g glucose) | Butanol selectivity (g/g total organic solvent) |
|---|---|---|---|
| Wild-type strains *C. actobutylicum* ATCC 824 | 9.7 | 0.17 | 0.65 |
| Recombinant strains *C. actobutylicum* ATCC 824 ΔeutD | 18.5 | 0.21 | 0.64 |
| Recombinant strains *C. actobutylicum* ATCC 824 ΔeutDΔbuk | 16.0 | 0.21 | 0.80 |
| Recombinant strains *Clostridium acetobutylicum* ATCC 824 ΔeutD Δbuk PptbAdh | 18.4 | 0.28 | 0.80 |
| Recombinant strains *Clostridium acetobutylicum* ATCC 824 ΔeutD Δbuk PthlAdh* | 19.0 | 0.29 | 0.83 |
| Recombinant strains *C. actobutylicum* ATCC 824 ΔeutD Δbuk ΔbukII PthlAdh* | 18.5 | 0.30 | 0.84 |
| Recombinant strains *C. actobutylicum* ATCC 824 ΔeutD Δbuk ΔbukII ΔctfB PthlAdh* | 18.6 | 0.30 | 0.83 |

As a result, as can be seen in Table 4 above, the recombinant strains *Clostridium acetobutylicum* ATCC 824 ΔeutD Δbuk PptbAdh, *Clostridium acetobutylicum* ATCC 824 ΔeutD Δbuk PthlAdh*, *C. actobutylicum* ATCC 824 ΔeutD Δbuk ΔbukII PthlAdh*, and *C. actobutylicum* ATCC 824 ΔeutD Δbuk ΔbukII ΔctfB PthlAdh* showed increases in butanol concentration, butanol yield and butanol selectivity. Specifically, these strains commonly showed a high butanol concentration of about 18 g/L or more, high butanol yield (0.28 g/g glucose or more) and high butanol selectivity (0.80 g/g total organic solvent or more).

Meanwhile, it can be seen that the recombinant strain *C. actobutylicum* ATCC 824 ΔeutDΔbuk is similar to the eutD-deleted mutant strain *C. actobutylicum* ATCC 824 ΔeutD in terms of yield. This is because acetic acid and butyrate are still produced even when both a gene in the butyrate-producing pathway and a gene in the acetic acid-producing pathway are deleted. In the present invention, this content was newly found, and thus the excellent butanol-producing strains as described above could be developed. The possible production of acetic acid by the role of CoA transferase was newly found by using the eutD-, buk (or/and bukII)- or ctfB-deleted strain of the present invention, thereby completing the present invention. As a result of manipulation of the metabolic flux, the above-described strains mostly have little or no butyrate and acetic acid at the end of fermentation.

INDUSTRIAL APPLICABILITY

The present invention provides recombinant microorganisms having a high ability to produce butanol with high selectivity, in which a specific gene was deleted or inactivated. The recombinant microorganisms according to the present invention do not substantially produce organic acids, including acetate and butyrate, and byproducts, including acetone, and can increase the hourly production of butanol. Thus, the recombinant microorganisms of the present invention are useful for the industrial production of butanol.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A recombinant microorganism having an increased ability to produce butanol, wherein an Adh* gene encoding alcohol/aldehyde dehydrogenase mutant having one or more mutations between 450 and 650 amino acid sequence of SEQ ID NO: 51 is amplified in the microorganism, and wherein the microorganism is *Clostridium acetobutylicum*.

2. A method for producing butanol, comprising the steps of:

culturing the recombinant microorganism of claim 1 to produce butanol; and recovering the produced butanol from the culture medium.

* * * * *

```
                       SEQUENCE LISTING

<160> NUMBER OF SEQ ID NOS: 51

<210> SEQ ID NO 1
<211> LENGTH: 69
<212> TYPE: DNA
<213> ORGANISM: Artificial Sequence
<220> FEATURE:
<223> OTHER INFORMATION: Synthetic Constuct

<400> SEQUENCE: 1
aattgcatgc taccgttcgt ataatgtatg ctatacgaag ttatcacacg gtttaacgac       60
ttaattacg                                                              69

<210> SEQ ID NO 2
<211> LENGTH: 70
<212> TYPE: DNA
<213> ORGANISM: Artificial Sequence
<220> FEATURE:
<223> OTHER INFORMATION: Synthetic Construct

<400> SEQUENCE: 2
atattctaga accgttcgta tagcatacat tatacgaagt tatccatgat tacgaattct       60
atgagtcgac                                                             70

<210> SEQ ID NO 3
<211> LENGTH: 36
<212> TYPE: DNA
<213> ORGANISM: Artificial Sequence
<220> FEATURE:
<223> OTHER INFORMATION: Synthetic Construct

<400> SEQUENCE: 3
aaaactgcag ccatggtcgc cagttaatag tttgcg                                36

<210> SEQ ID NO 4
<211> LENGTH: 30
<212> TYPE: DNA
<213> ORGANISM: Artificial Sequence
<220> FEATURE:
<223> OTHER INFORMATION: Synthetic Construct

<400> SEQUENCE: 4 aaacccggg cgccgcatac actattctca                                        30

<210> SEQ ID NO 5
```

```
<211> LENGTH: 64
<212> TYPE: DNA
<213> ORGANISM: Artificial Sequence
<220> FEATURE:
<223> OTHER INFORMATION: Synthetic Construct

<400> SEQUENCE: 5
gcatggatcc agaatttaaa aggagggatt aaatctagaa tgataagaag catgacggga    60
tttg                                                                64

<210> SEQ ID NO 6
<211> LENGTH: 36
<212> TYPE: DNA
<213> ORGANISM: Artificial Sequence
<220> FEATURE:
<223> OTHER INFORMATION: Synthetic Construct

<400> SEQUENCE: 6
gcatggcgcc tcactctata ttttgaattt gttctc                              36

<210> SEQ ID NO 7
<211> LENGTH: 33
<212> TYPE: DNA
<213> ORGANISM: Artificial Sequence
<220> FEATURE:
<223> OTHER INFORMATION: Synthetic Construct

<400> SEQUENCE: 7
gcaatctaga atgtccaatt tactgaccgt aca                                 33

<210> SEQ ID NO 8
<211> LENGTH: 32
<212> TYPE: DNA
<213> ORGANISM: Artificial Sequence
<220> FEATURE:
<223> OTHER INFORMATION: Synthetic Construct

<400> SEQUENCE: 8
gcatggcgcc ctaatcgcca tcttccagca gg                                  32

<210> SEQ ID NO 9
<211> LENGTH: 31
<212> TYPE: DNA
<213> ORGANISM: Artificial Sequence
<220> FEATURE:
<223> OTHER INFORMATION: Synthetic Construct

<400> SEQUENCE: 9
ctagccatgg agcatatggg agtgtgctaa g                                   31

<210> SEQ ID NO 10
<211> LENGTH: 30
<212> TYPE: DNA
<213> ORGANISM: Artificial Sequence
<220> FEATURE:
<223> OTHER INFORMATION: Synthetic Construct

<400> SEQUENCE: 10
cggccaacgc tcgcagtcag gtattatcat                                     30

<210> SEQ ID NO 11
<211> LENGTH: 36
<212> TYPE: DNA
<213> ORGANISM: Artificial Sequence
<220> FEATURE:
<223> OTHER INFORMATION: Synthetic Construct
```

<400> SEQUENCE: 11
gcgaatggcg agatgaacta gctgatattg ctataa                                    36

<210> SEQ ID NO 12
<211> LENGTH: 35
<212> TYPE: DNA
<213> ORGANISM: Artificial Sequence
<220> FEATURE:
<223> OTHER INFORMATION: Synthetic Construct

<400> SEQUENCE: 12
acgtcccggg cgagtacagt ttcatccttc atatc                                     35

<210> SEQ ID NO 13
<211> LENGTH: 26
<212> TYPE: DNA
<213> ORGANISM: Artificial Sequence
<220> FEATURE:
<223> OTHER INFORMATION: Synthetic Construct

<400> SEQUENCE: 13
ctgactgcga gcgttggccg attcat                                               26

<210> SEQ ID NO 14
<211> LENGTH: 26
<212> TYPE: DNA
<213> ORGANISM: Artificial Sequence
<220> FEATURE:
<223> OTHER INFORMATION: Synthetic Construct

<400> SEQUENCE: 14
tagttcatct cgccattcgc cattca                                               26

<210> SEQ ID NO 15
<211> LENGTH: 22
<212> TYPE: DNA
<213> ORGANISM: Artificial Sequence
<220> FEATURE:
<223> OTHER INFORMATION: Synthetic Construct

<400> SEQUENCE: 15
gaggataaag aatatacgca gg                                                   22

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct

<400> SEQUENCE: 16
ttgccgtcct aaactctgaa                                                      20

<210> SEQ ID NO 17
<211> LENGTH: 22
<212> TYPE: DNA
<213> ORGANISM: Artificial Sequence
<220> FEATURE:
<223> OTHER INFORMATION: Synthetic Construct

<400> SEQUENCE: 17
cttcctttgg caattcaagt tc                                                   22

<210> SEQ ID NO 18

```
<211> LENGTH: 20
<212> TYPE: DNA
<213> ORGANISM: Artificial Sequence
<220> FEATURE:
<223> OTHER INFORMATION: Synthetic Construct

<400> SEQUENCE: 18
gtggattatg aagcggtgca                                                   20

<210> SEQ ID NO 19
<211> LENGTH: 31
<212> TYPE: DNA
<213> ORGANISM: Artificial Sequence
<220> FEATURE:
<223> OTHER INFORMATION: Synthetic Construct

<400> SEQUENCE: 19
ctagccatgg atgtatagat tactaataat c                                      31

<210> SEQ ID NO 20
<211> LENGTH: 31
<212> TYPE: DNA
<213> ORGANISM: Artificial Sequence
<220> FEATURE:
<223> OTHER INFORMATION: Synthetic Construct

<400> SEQUENCE: 20
cggccaacgc ctatttcatt tgcaataatt c                                      31

<210> SEQ ID NO 21
<211> LENGTH: 32
<212> TYPE: DNA
<213> ORGANISM: Artificial Sequence
<220> FEATURE:
<223> OTHER INFORMATION: Synthetic Construct

<400> SEQUENCE: 21
gcgaatggcg ccaagaaaaa gtatattcca tg                                     32

<210> SEQ ID NO 22
<211> LENGTH: 32
<212> TYPE: DNA
<213> ORGANISM: Artificial Sequence
<220> FEATURE:
<223> OTHER INFORMATION: Synthetic Construct

<400> SEQUENCE: 22
acgtcccggg cttctcctct taaaactcta ag                                     32

<210> SEQ ID NO 23
<211> LENGTH: 32
<212> TYPE: DNA
<213> ORGANISM: Artificial Sequence
<220> FEATURE:
<223> OTHER INFORMATION: Synthetic Construct

<400> SEQUENCE: 23
attgcaaatg aaatagcgcc attcgccatt ca                                     32

<210> SEQ ID NO 24
<211> LENGTH: 31
<212> TYPE: DNA
<213> ORGANISM: Artificial Sequence
<220> FEATURE:
<223> OTHER INFORMATION: Synthetic Construct

<400> SEQUENCE: 24
``` tatactttt cttgggcgtt ggccgattca t                                        31

<210> SEQ ID NO 25
<211> LENGTH: 33
<212> TYPE: DNA
<213> ORGANISM: Artificial Sequence
<220> FEATURE:
<223> OTHER INFORMATION: Synthetic Construct

<400> SEQUENCE: 25
ctagccatgg ggactttatt atgaaattta aac                                     33

<210> SEQ ID NO 26
<211> LENGTH: 31
<212> TYPE: DNA
<213> ORGANISM: Artificial Sequence
<220> FEATURE:
<223> OTHER INFORMATION: Synthetic Construct

<400> SEQUENCE: 26
cggccaacgc cactatatat gctgacactc c                                       31

<210> SEQ ID NO 27
<211> LENGTH: 32
<212> TYPE: DNA
<213> ORGANISM: Artificial Sequence
<220> FEATURE:
<223> OTHER INFORMATION: Synthetic Construct

<400> SEQUENCE: 27
gcgaatggcg ctggaatacc tgaacttcct ag                                      32

<210> SEQ ID NO 28
<211> LENGTH: 31
<212> TYPE: DNA
<213> ORGANISM: Artificial Sequence
<220> FEATURE:
<223> OTHER INFORMATION: Synthetic Construct

<400> SEQUENCE: 28
acgtcccggg aacccttaag gttccttctg c                                       31

<210> SEQ ID NO 29
<211> LENGTH: 32
<212> TYPE: DNA
<213> ORGANISM: Artificial Sequence
<220> FEATURE:
<223> OTHER INFORMATION: Synthetic Construct

<400> SEQUENCE: 29
gtcagcatat atagtgcgcc attcgccatt ca                                      32

<210> SEQ ID NO 30
<211> LENGTH: 32
<212> TYPE: DNA
<213> ORGANISM: Artificial Sequence
<220> FEATURE:
<223> OTHER INFORMATION: Synthetic Construct

<400> SEQUENCE: 30
agttcaggta ttccaggcgt tggccgattc at                                      32

<210> SEQ ID NO 31
<211> LENGTH: 31
<212> TYPE: DNA

<213> ORGANISM: Artificial Sequence
<220> FEATURE:
<223> OTHER INFORMATION: Synthetic Construct

<400> SEQUENCE: 31
ctagccatgg tccctatatg gcaatggcag c                              31

<210> SEQ ID NO 32
<211> LENGTH: 30
<212> TYPE: DNA
<213> ORGANISM: Artificial Sequence
<220> FEATURE:
<223> OTHER INFORMATION: Synthetic Construct

<400> SEQUENCE: 32
cggccaacgc ttaggactag cgcccattcc                                30

<210> SEQ ID NO 33
<211> LENGTH: 32
<212> TYPE: DNA
<213> ORGANISM: Artificial Sequence
<220> FEATURE:
<223> OTHER INFORMATION: Synthetic Construct

<400> SEQUENCE: 33
gcgaatggcg ggaggagact atacaacagt ac                             32

<210> SEQ ID NO 34
<211> LENGTH: 33
<212> TYPE: DNA
<213> ORGANISM: Artificial Sequence
<220> FEATURE:
<223> OTHER INFORMATION: Synthetic Construct

<400> SEQUENCE: 34
acgtcccggg ttctttctaa acagccatgg gtc                            33

<210> SEQ ID NO 35
<211> LENGTH: 31
<212> TYPE: DNA
<213> ORGANISM: Artificial Sequence
<220> FEATURE:
<223> OTHER INFORMATION: Synthetic Construct

<400> SEQUENCE: 35
gggcgctagt cctaacgcca ttcgccattc a                              31

<210> SEQ ID NO 36
<211> LENGTH: 32
<212> TYPE: DNA
<213> ORGANISM: Artificial Sequence
<220> FEATURE:
<223> OTHER INFORMATION: Synthetic Construct

<400> SEQUENCE: 36
ttgtatagtc tcctccgcgt tggccgattc at                             32

<210> SEQ ID NO 37
<211> LENGTH: 31
<212> TYPE: DNA
<213> ORGANISM: Artificial Sequence
<220> FEATURE:
<223> OTHER INFORMATION: Synthetic Construct

<400> SEQUENCE: 37
atagtcgaca tgaaagtcac aacagtaaag g                              31

<210> SEQ ID NO 38
<211> LENGTH: 30
<212> TYPE: DNA
<213> ORGANISM: Artificial Sequence
<220> FEATURE:
<223> OTHER INFORMATION: Synthetic Construct

<400> SEQUENCE: 38
cgcgaattct taaggttgtt ttttaaaaca                                    30

<210> SEQ ID NO 39
<211> LENGTH: 24
<212> TYPE: DNA
<213> ORGANISM: Artificial Sequence
<220> FEATURE:
<223> OTHER INFORMATION: Synthetic Construct

<400> SEQUENCE: 39
tatctgcagt gtggatggag ttaa                                          24

<210> SEQ ID NO 40
<211> LENGTH: 24
<212> TYPE: DNA
<213> ORGANISM: Artificial Sequence
<220> FEATURE:
<223> OTHER INFORMATION: Synthetic Construct

<400> SEQUENCE: 40
attgtcgact ttaatccctc cttt                                          24

<210> SEQ ID NO 41
<211> LENGTH: 35
<212> TYPE: DNA
<213> ORGANISM: Artificial Sequence
<220> FEATURE:
<223> OTHER INFORMATION: Synthetic Construct

<400> SEQUENCE: 41
cgcgaattcg ggcccatatc caatgaactt agacc                              35

<210> SEQ ID NO 42
<211> LENGTH: 27
<212> TYPE: DNA
<213> ORGANISM: Artificial Sequence
<220> FEATURE:
<223> OTHER INFORMATION: Synthetic Construct

<400> SEQUENCE: 42
caccatatgg cctagagctg aagttat                                       27

<210> SEQ ID NO 43
<211> LENGTH: 35
<212> TYPE: DNA
<213> ORGANISM: Artificial Sequence
<220> FEATURE:
<223> OTHER INFORMATION: Synthetic Construct

<400> SEQUENCE: 43
aaaactgcag tttatgaaag tcacaacagt aaagg                              35

<210> SEQ ID NO 44
<211> LENGTH: 38
<212> TYPE: DNA
<213> ORGANISM: Artificial Sequence
<220> FEATURE:

```
<223> OTHER INFORMATION: Synthetic Construct

<400> SEQUENCE: 44
taaattatag gggtcactac cagtaactat aaaggctc                              38

<210> SEQ ID NO 45
<211> LENGTH: 38
<212> TYPE: DNA
<213> ORGANISM: Artificial Sequence
<220> FEATURE:
<223> OTHER INFORMATION: Synthetic Construct

<400> SEQUENCE: 45
gagcctttat agttactggt agtgaccccct ataattta                             38

<210> SEQ ID NO 46
<211> LENGTH: 35
<212> TYPE: DNA
<213> ORGANISM: Artificial Sequence
<220> FEATURE:
<223> OTHER INFORMATION: Synthetic Construct

<400> SEQUENCE: 46
cccccggggg gttgaaatat gaaggtttaa ggttg                                 35

<210> SEQ ID NO 47
<211> LENGTH: 36
<212> TYPE: DNA
<213> ORGANISM: Artificial Sequence
<220> FEATURE:
<223> OTHER INFORMATION: Synthetic Construct

<400> SEQUENCE: 47
ggccccaagc ttagaatgaa gtttcttatg cacaag                                36

<210> SEQ ID NO 48
<211> LENGTH: 36
<212> TYPE: DNA
<213> ORGANISM: Artificial Sequence
<220> FEATURE:
<223> OTHER INFORMATION: Synthetic Construct

<400> SEQUENCE: 48
aaactgcagt ctaactaacc tcctaaattt tgatac                                36

<210> SEQ ID NO 49
<211> LENGTH: 31
<212> TYPE: DNA
<213> ORGANISM: Artificial Sequence
<220> FEATURE:
<223> OTHER INFORMATION: Synthetic Construct

<400> SEQUENCE: 49
ccaagcttcg acttttttaac aaaatatatt g                                    31

<210> SEQ ID NO 50
<211> LENGTH: 32
<212> TYPE: DNA
<213> ORGANISM: Artificial Sequence
<220> FEATURE:
<223> OTHER INFORMATION: Synthetic Construct

<400> SEQUENCE: 50
ccaagcttga cattaaaaaa ataagagtta cc                                    32
```

-continued

```
<210> SEQ ID NO 51
<211> LENGTH: 862
<212> TYPE: PRT
<213> ORGANISM: Artificial Sequence
<220> FEATURE:
<223> OTHER INFORMATION: Synthetic Construct

<400> SEQUENCE: 51
```

| Met | Lys | Val | Thr | Thr | Val | Lys | Glu | Leu | Asp | Glu | Lys | Leu | Lys | Val | Ile |
|---|---|---|---|---|---|---|---|---|---|---|---|---|---|---|---|
| 1 | | | | 5 | | | | | 10 | | | | | 15 | |

Lys Glu Ala Gln Lys Lys Phe Ser Cys Tyr Ser Gln Glu Met Val Asp
          20                25                30

Glu Ile Phe Arg Asn Ala Ala Met Ala Ala Ile Asp Ala Arg Ile Glu
          35                40                45

Leu Ala Lys Ala Ala Val Leu Glu Thr Gly Met Gly Leu Val Glu Asp
50                  55                  60

Lys Val Ile Lys Asn His Phe Ala Gly Glu Tyr Ile Tyr Asn Lys Tyr
65                      70                  75                  80

Lys Asp Glu Lys Thr Cys Gly Ile Ile Glu Arg Asn Glu Pro Tyr Gly
                85                  90                  95

Ile Thr Lys Ile Ala Glu Pro Ile Gly Val Val Ala Ala Ile Ile Pro
            100                 105                 110

Val Thr Asn Pro Thr Ser Thr Thr Ile Phe Lys Ser Leu Ile Ser Leu
            115                 120                 125

Lys Thr Arg Asn Gly Ile Phe Phe Ser Pro His Pro Arg Ala Lys Lys
        130                 135                 140

Ser Thr Ile Leu Ala Ala Lys Thr Ile Leu Asp Ala Ala Val Lys Ser
145                 150                 155                 160

Gly Ala Pro Glu Asn Ile Ile Gly Trp Ile Asp Glu Pro Ser Ile Glu
                165                 170                 175

Leu Thr Gln Tyr Leu Met Gln Lys Ala Asp Ile Thr Leu Ala Thr Gly
            180                 185                 190

Gly Pro Ser Leu Val Lys Ser Ala Tyr Ser Ser Gly Lys Pro Ala Ile
            195                 200                 205

Gly Val Gly Pro Gly Asn Thr Pro Val Ile Ile Asp Glu Ser Ala His
        210                 215                 220

Ile Lys Met Ala Val Ser Ser Ile Ile Leu Ser Lys Thr Tyr Asp Asn
225                 230                 235                 240

Gly Val Ile Cys Ala Ser Glu Gln Ser Val Ile Val Leu Lys Ser Ile
                245                 250                 255

Tyr Asn Lys Val Lys Asp Glu Phe Gln Glu Arg Gly Ala Tyr Ile Ile
            260                 265                 270

Lys Lys Asn Glu Leu Asp Lys Val Arg Glu Val Ile Phe Lys Asp Gly
            275                 280                 285

Ser Val Asn Pro Lys Ile Val Gly Gln Ser Ala Tyr Thr Ile Ala Ala
        290                 295                 300

Met Ala Gly Ile Lys Val Pro Lys Thr Thr Arg Ile Leu Ile Gly Glu
305                 310                 315                 320

Val Thr Ser Leu Gly Glu Glu Pro Phe Ala His Glu Lys Leu Ser
                325                 330                 335

Pro Val Leu Ala Met Tyr Glu Ala Asp Asn Phe Asp Asp Ala Leu Lys
            340                 345                 350

Lys Ala Val Thr Leu Ile Asn Leu Gly Gly Leu Gly His Thr Ser Gly
        355                 360                 365

Ile Tyr Ala Asp Glu Ile Lys Ala Arg Asp Lys Ile Asp Arg Phe Ser

```
                370                 375                 380
Ser Ala Met Lys Thr Val Arg Thr Phe Val Asn Ile Pro Thr Ser Gln
385                 390                 395                 400

Gly Ala Ser Gly Asp Leu Tyr Asn Phe Arg Ile Pro Pro Ser Phe Thr
                405                 410                 415

Leu Gly Cys Gly Phe Trp Gly Gly Asn Ser Val Ser Glu Asn Val Gly
                420                 425                 430

Pro Lys His Leu Leu Asn Ile Lys Thr Val Ala Glu Arg Arg Glu Asn
                435                 440                 445

Met Leu Trp Phe Arg Val Pro His Lys Val Tyr Phe Lys Phe Gly Cys
                450                 455                 460

Leu Gln Phe Ala Leu Lys Asp Leu Lys Asp Leu Lys Lys Arg Ala
465                 470                 475                 480

Phe Ile Val Thr Asp Ser Asp Pro Tyr Asn Leu Asn Tyr Val Asp Ser
                485                 490                 495

Ile Ile Lys Ile Leu Glu His Leu Asp Ile Asp Phe Lys Val Phe Asn
                500                 505                 510

Lys Val Gly Arg Glu Ala Asp Leu Lys Thr Ile Lys Lys Ala Thr Glu
                515                 520                 525

Glu Met Ser Ser Phe Met Pro Asp Thr Ile Ile Ala Leu Gly Gly Thr
                530                 535                 540

Pro Glu Met Ser Ser Ala Lys Leu Met Trp Val Leu Tyr Glu His Pro
545                 550                 555                 560

Glu Val Lys Phe Glu Asp Leu Ala Ile Lys Phe Met Asp Ile Arg Lys
                565                 570                 575

Arg Ile Tyr Thr Phe Pro Lys Leu Gly Lys Ala Met Leu Val Ala
                580                 585                 590

Ile Thr Thr Ser Ala Gly Ser Gly Ser Glu Val Thr Pro Phe Ala Leu
                595                 600                 605

Val Thr Asp Asn Asn Thr Gly Asn Lys Tyr Met Leu Ala Asp Tyr Glu
                610                 615                 620

Met Thr Pro Asn Met Ala Ile Val Asp Ala Glu Leu Met Met Lys Met
625                 630                 635                 640

Pro Lys Gly Leu Thr Ala Tyr Ser Gly Ile Asp Ala Leu Val Asn Ser
                645                 650                 655

Ile Glu Ala Tyr Thr Ser Val Tyr Ala Ser Glu Tyr Thr Asn Gly Leu
                660                 665                 670

Ala Leu Glu Ala Ile Arg Leu Ile Phe Lys Tyr Leu Pro Glu Ala Tyr
                675                 680                 685

Lys Asn Gly Arg Thr Asn Glu Lys Ala Arg Glu Lys Met Ala His Ala
                690                 695                 700

Ser Thr Met Ala Gly Met Ala Ser Ala Asn Ala Phe Leu Gly Leu Cys
705                 710                 715                 720

His Ser Met Ala Ile Lys Leu Ser Ser Glu His Asn Ile Pro Ser Gly
                725                 730                 735

Ile Ala Asn Ala Leu Leu Ile Glu Glu Val Ile Lys Phe Asn Ala Val
                740                 745                 750

Asp Asn Pro Val Lys Gln Ala Pro Cys Pro Gln Tyr Lys Tyr Pro Asn
                755                 760                 765

Thr Ile Phe Arg Tyr Ala Arg Ile Ala Asp Tyr Ile Lys Leu Gly Gly
                770                 775                 780

Asn Thr Asp Glu Glu Lys Val Asp Leu Leu Ile Asn Lys Ile His Glu
785                 790                 795                 800
```

```
Leu Lys Lys Ala Leu Asn Ile Pro Thr Ser Ile Lys Asp Ala Gly Val
            805                 810                 815

Leu Glu Glu Asn Phe Tyr Ser Ser Leu Asp Arg Ile Ser Glu Leu Ala
            820                 825                 830

Leu Asp Asp Gln Cys Thr Gly Ala Asn Pro Arg Phe Pro Leu Thr Ser
        835                 840                 845

Glu Ile Lys Glu Met Tyr Ile Asn Cys Phe Lys Lys Gln Pro
    850                 855                 860
```